United States Patent
Van De Waterbeemd et al.

(10) Patent No.: US 9,272,006 B2
(45) Date of Patent: Mar. 1, 2016

(54) PROCESS FOR DETERGENT-FREE PRODUCTION OF OUTER MEMBRANE VESICLES OF A GRAM-NEGATIVE BACTERIUM

(75) Inventors: Bas Van De Waterbeemd, Utrecht (NL); Leonardus Aldolfus Van Der Pol, Groningen (NL)

(73) Assignee: DE STAAT DER NEDERLANDEN, VERT. DOOR DE MINISTER VAN VWS MINISTERIE VAN VOLKSGEZONDHEID, WELZIJN EN SPORT, The Hague (NL)

( * ) Notice: Subject to any disclaimer, the term of this patent is extended or adjusted under 35 U.S.C. 154(b) by 0 days.

(21) Appl. No.: 14/131,279

(22) PCT Filed: Jul. 5, 2012

(86) PCT No.: PCT/NL2012/050478
§ 371 (c)(1),
(2), (4) Date: Jan. 7, 2014

(87) PCT Pub. No.: WO2013/006055
PCT Pub. Date: Jan. 10, 2013

(65) Prior Publication Data
US 2014/0147469 A1 May 29, 2014

Related U.S. Application Data

(60) Provisional application No. 61/505,221, filed on Jul. 7, 2011.

(30) Foreign Application Priority Data

Jul. 7, 2011 (EP) .................................... 11173085

(51) Int. Cl.
*C12N 1/00* (2006.01)
*A61K 35/74* (2015.01)
*A61K 39/095* (2006.01)
*A61K 39/00* (2006.01)

(52) U.S. Cl.
CPC .............. *A61K 35/74* (2013.01); *A61K 39/095* (2013.01); *A61K 2039/55505* (2013.01); *A61K 2039/70* (2013.01)

(58) Field of Classification Search
CPC ...................................................... A61K 35/74
See application file for complete search history.

(56) References Cited

U.S. PATENT DOCUMENTS

2003/0059444 A1  3/2003  Zollinger et al.
2011/0033500 A1  2/2011  Biemans et al.

OTHER PUBLICATIONS

D. Post et al."Biochemical and functional characterization of membrane blebs purified from Neisseria meningitidis serogroup B", Journal of Biological Chemistry 280 (46):38383-38394, (2005).
N. B. Saunders et al., "Immunogenicity of intranasally administered meningococcal native outer membrane vesicles in mice",Infection and Immunity, 67(1):113-199 (1999).
B. Van De Waterbeemd et al. "Improved OMV vaccine against Neisseria meningitidis using genetically engineered strains and a detergent-free purification process", Vaccine, 28(30) 4810-4816 (2010).
Van Den Dobbelsteen et al., "Immunogeneic of a combination vaccine containing pneumococcal conjugates and meningococcal PorA OMV", Vaccine, 25(13):2491-2496 (2007).
P. Van Der Ley et al., "Next-generation outer membrane vesicle vaccines against Neisseria meningitidis based on nontoxic LPS mutants", Human Vaccines, 7(8):886-890 (2011).
W.D. Zollinger et al., "Design and evaluation in mice of a broadly protective meningococcal group B native outer membrane vesicle vaccine", Vaccine 28(31):5057-5067 (2010).
Van De Waterbeemd et al., Identification and optizmization of critical process parameters for the production of NOMV vaccine against Neisseria meningitidis, Vaccine 30:3683-3690 (2012).

*Primary Examiner* — Albert Navarro
(74) *Attorney, Agent, or Firm* — Browdy and Neimark, PLLC

(57) ABSTRACT

The present invention relates to the fields of medical microbiology and vaccines. In particular the invention relates to a process for detergent-free preparation of outer membrane vesicles (OMV) of Gram negative bacteria for use in vaccines, to OMV obtainable by said process, and to a pharmaceutical composition comprising such OMV. The present invention further relates to the use of OMV of the present invention as a medicament in particular for use in a method for eliciting an immune response.

16 Claims, 2 Drawing Sheets

SEQUENCE LISTING

<160> NUMBER OF SEQ ID NOS: 2

<210> SEQ ID NO 1
<211> LENGTH: 299
<212> TYPE: PRT
<213> ORGANISM: Neisseria meningitidis

<400> SEQUENCE: 1

Met Pro Ser Glu Lys Lys Met Cys Ile Glu Met Lys Phe Ile Phe Phe
1               5                   10                  15

Val Leu Tyr Val Leu Gln Phe Leu Pro Phe Ala Leu Leu His Lys Ile
            20                  25                  30

Ala Asp Leu Thr Gly Leu Leu Ala Tyr Leu Leu Val Lys Pro Arg Arg
        35                  40                  45

Arg Ile Gly Glu Ile Asn Leu Ala Lys Cys Phe Ser Glu Trp Ser Glu
50                  55                  60

Glu Lys Arg Lys Thr Val Leu Lys Gln His Phe Lys His Met Ala Lys
65                  70                  75                  80

Leu Met Leu Glu Tyr Gly Leu Tyr Trp Tyr Ala Pro Ala Gly Arg Leu
                85                  90                  95

Lys Ser Leu Val Arg Tyr Arg Asn Lys His Tyr Leu Asp Asp Ala Leu
            100                 105                 110

Ala Ala Gly Glu Lys Val Ile Ile Leu Tyr Pro His Phe Thr Ala Phe
        115                 120                 125

Glu Met Ala Val Tyr Ala Leu Asn Gln Asp Ile Pro Leu Ile Ser Met
130                 135                 140

Tyr Ser His Gln Lys Asn Lys Ile Leu Asp Glu Gln Ile Leu Lys Gly
145                 150                 155                 160

Arg Asn Arg Tyr His Asn Val Phe Leu Ile Gly Arg Thr Glu Gly Leu
                165                 170                 175

Arg Ala Leu Val Lys Gln Phe Arg Lys Ser Ala Pro Phe Leu Tyr
            180                 185                 190

Leu Pro Asp Gln Asp Phe Gly Arg Asn Asp Ser Val Phe Val Asp Phe
        195                 200                 205

Phe Gly Ile Gln Thr Ala Thr Ile Thr Gly Leu Ser Arg Ile Ala Ala
210                 215                 220

Leu Ala Asn Ala Lys Val Ile Pro Ala Ile Pro Val Arg Glu Ala Asp
225                 230                 235                 240

Asn Thr Val Thr Leu His Phe Tyr Pro Ala Trp Lys Ser Phe Pro Gly
                245                 250                 255

Glu Asp Ala Lys Ala Asp Ala Gln Arg Met Asn Arg Phe Ile Glu Asp
            260                 265                 270

Arg Val Arg Glu His Pro Gln Tyr Phe Trp Leu His Lys Arg Phe
        275                 280                 285

Lys Thr Arg Pro Glu Gly Ser Pro Asp Phe Tyr
290                 295

<210> SEQ ID NO 2
<211> LENGTH: 242
<212> TYPE: PRT
<213> ORGANISM: Neisseria meningitidis

<400> SEQUENCE: 2

Met Thr Lys Gln Leu Lys Leu Ser Ala Leu Phe Val Ala Leu Leu Ala
1               5                   10                  15

Ser Gly Thr Ala Val Ala Gly Glu Ala Ser Val Gln Gly Tyr Thr Val
            20                  25                  30

Ser Gly Gln Ser Asn Glu Ile Val Arg Asn Asn Tyr Gly Glu Cys Trp
        35                  40                  45

Lys Asn Ala Tyr Phe Asp Lys Ala Ser Gln Gly Arg Val Glu Cys Gly
50                  55                  60

-continued

```
Asp Ala Val Ala Ala Pro Glu Pro Glu Pro Glu Pro Ala Pro
65              70              75              80

Ala Pro Val Val Val Glu Gln Ala Pro Gln Tyr Val Asp Glu Thr
            85              90              95

Ile Ser Leu Ser Ala Lys Thr Leu Phe Gly Phe Asp Lys Asp Ser Leu
            100             105             110

Arg Ala Glu Ala Gln Asp Asn Leu Lys Val Leu Ala Gln Arg Leu Ser
        115             120             125

Arg Thr Asn Val Gln Ser Val Arg Val Glu Gly His Thr Asp Phe Met
        130             135             140

Gly Ser Asp Lys Tyr Asn Gln Ala Leu Ser Glu Arg Arg Ala Tyr Val
145             150             155             160

Val Ala Asn Asn Leu Val Ser Asn Gly Val Pro Val Ser Arg Ile Ser
            165             170             175

Ala Val Gly Leu Gly Glu Ser Gln Ala Gln Met Thr Gln Val Cys Glu
            180             185             190

Ala Glu Val Ala Lys Leu Gly Ala Lys Val Ser Lys Ala Lys Lys Arg
        195             200             205

Glu Ala Leu Ile Ala Cys Ile Glu Pro Asp Arg Arg Val Asp Val Lys
        210             215             220

Ile Arg Ser Ile Val Thr Arg Gln Val Val Pro Ala His Asn His His
225             230             235             240

Gln His
```

PROCESS FOR DETERGENT-FREE PRODUCTION OF OUTER MEMBRANE VESICLES OF A GRAM-NEGATIVE BACTERIUM

FIELD OF THE INVENTION

The present invention relates to the fields of medical microbiology and vaccines. In particular the invention relates to a process for detergent-free preparation of outer membrane vesicles (OMV) of Gram negative bacteria for use in vaccines, to OMV obtainable by said process, and to a pharmaceutical composition comprising such OMV. The present invention further relates to the use of OMV of the present invention as a medicament in particular for use in a method for eliciting an immune response.

BACKGROUND OF THE INVENTION

*Neisseria meningitidis* is a human pathogen that can cause acute meningitis and septicemia, with fatality rates around 15% [Girard et al, 2006]. Serogroup B meningitis accounts for 30-40% of meningitis cases in North America [Sharip et al, 2006; Kaplan et al, 2006] and up to 80% in some European countries [Trotter et al, 2007; Gray et al, 2006], yet a broadly protective vaccine is not available. Effective vaccines against other serogroups have been developed based on capsular polysaccharide conjugated to a carrier protein [Snape et al, 2008]. This approach was not feasible for serogroup B, due to poor immunogenicity [Morley et al, 2001] and concerns for vaccination-induced autoimmunity [Finne et al, 1983]. To date, vaccines based on outer membrane vesicles (OMV) are the only vaccines that successfully controlled serogroup B epidemics with examples in Norway, Cuba, and New Zealand [Bjune et al, 1991; Thornton et al, 2006; Martin et al, 1998; Sierra et al, Fredriksen et al, 1991].

OMV are released from the outer membrane of gram negative bacteria and consist of a phospholipid (PL) bilayer that contains outer membrane proteins, lipopolysacchharide (LPS) and periplasmic constituents [Deatherage et al, 2009]. PorA protein was identified as the major protective antigen in OMV, but is highly variable between the circulating serogroup B strains which complicates vaccine development [Saukkonen et al, 1989; Martin et al, 2006]. For this reason, Rijks Instituut voor Volksgezondheid en Milieu (RWM), i.e the National Institute for Public Health and the Environment (Bilthoven, The Netherlands) developed an OMV vaccine based on genetically modified *N. meningitidis* strains that express multiple PorA subtypes. This multivalent OMV vaccine was initially made with 2 trivalent PorA strains, expressing a total of 6 PorA subtypes [van der Ley et al, 1995; Claassen et al, 1996] and provided functional immunogenicity in phase II clinical trials. To ensure sufficient coverage for serogroup B strains circulating globally, a third trivalent strain was added [van den Dobbelsteen et al, 2007].

OMV vaccines are traditionally prepared with detergent extraction (dOMV purification process) to remove LPS and increase vesicle release. The LPS of *N. meningitidis* is highly toxic, but residual amounts (approx. 1%) are needed to maintain vesicle structure and adjuvate the immune response against PorA [Arigita et al, 2005; Arigita et al, 2003; Steeghs et al, 2004]. With balanced detergent concentrations the dOMV purification process provides these requirements, however there are major disadvantages. Along with LPS, detergent removes PL and also lipoproteins that contribute to immunogenicity, such as factor H binding protein [Koeberling et al, 2009; Koeberling et al, 2008]. The resulting immune response is directed against a specific PorA subtype, without eliciting cross-protection [Morley et al, 2001; van der Voort et al, 1996]. In addition, selective removal of LPS and PL changes the native vesicle structure and promotes aggregation [Hoist et al, 2009; Cametti et al, 2008]. Detergent-treatment is necessary to decrease LPS toxicity, but has detrimental side effects that complicate vaccine development.

Detergent-free OMV purification processes retain all LPS, resulting not only in a preserved native vesicle structure, but also in vaccines that are inherently toxic when used for parenteral immunization [Hoist et al, 2009]. Two detergent-free purification processes have been described. The native OMV (nOMV) process [Zollinger et al 1979; U.S. Pat. No. 6,558,677] comprises similar steps as dOMV, however with a detergent-free extraction step and the supernatant OMV (sOMV) process [Post et al, 2005; Devoe et al, 1973; Hoekstra et al, 1976] utilizes ultrafiltration or ultracentrifugation to purify spontaneously released OMV from the culture supernatant, without extraction. nOMV vaccines produced encouraging results in animals and humans, but high LPS content limited applicability of the vaccine to intranasal administration [Guthrie et al, 2004; Katial et al, 2002; Saunders et al, 1999; Drabick et al, 1999]. Preclinical data on sOMV vaccines is limited to a single study in mice, reporting cross-protection against a panel of serogroup B strains that was not found with dOMV, however potential differences in toxicity and stability were not addressed [Ferrari et al, 2006]. The sOMV process imposes an additional challenge, since it produces OMV yields that are too low for feasible process development [Post et al, 2005; Devoe et al, 1973].

Discovery of lpxL1 mutant strains at RIVM Bilthoven [van der Ley et al, 2001] provided a solution for the LPS toxicity issue. Deletion of lpxL1 attenuate LPS toxicity, while preserving the adjuvant activity needed for the immune response [Koeberling et al, 2008; van der Ley et al, 2001; Fisseha et al, 2005; van de Waterbeemd et al, 2010].

However, for clinical trials or GMP manufacturing of nOMV/sOMV a robust scalable production process is required in which the EDTA extraction step is needed for high yield, but to date causes undesired effects such as bacterial lysis [Prachayasittikul et al, 2010]. DNA release caused by lysis is a problem for large scale production since removal processes such as ultracentrifugation only have limited capacity.

Accordingly, since the processes available to date to prepare sOMV and nOMV either suffer from low yield and/or low purity and/or are limited to laboratory scale, there is a need for improved processes to prepare bacterial OMV, in particular for processes at industrial scale.

DESCRIPTION OF THE INVENTION

Surprisingly, it has now been demonstrated that OMV can be prepared detergent-free with high yield and high purity in a process that can be performed at any scale.

Accordingly, in a first aspect the present invention provides a process for detergent-free preparation of bacterial outer membrane vesicles (OMV) for use in vaccines, said process comprising the steps of:
  a) cultivating a population of a Gram-negative bacterium to stationary growth phase;
  b) at a time point at least about 1 hour after onset of stationary growth phase, incubating the bacteria obtained in a) in a medium adjusted to or having a pH higher than about pH 7.5 or higher than pH 8.0 and a concentration of a metal chelating agent, preferably EDTA, of between about 1 and 100 mM to extract OMV; and, c) recovering the OMV extracted in b), wherein the recovery at least comprises removal of the bacteria from the OMV.

Preferably, the time point after the onset of stationary phase of about 1 hours is a time point of between 1 and 9 hours, more preferably between, 1 and 8 hours, 1 and 7 hours, 1 and 6 hours, 2 and 5 hours, 2 and 4 hours, 2 and 3.5 hours or 2.5 and 3.5 hours.

Preferably, in any of the processes according to the invention, the OMV are sterilized, preferably by filter sterilization, preferably using a filter with pores of less than about 0.3 micrometer. Preferably, sterilization is performed during step c); yield loss is greatly decreased due to performing step b) according to the invention. Filter sterilization also referred to as sterile filtration, is herein defined as filtering a compound of interest through a filter, preferably with pores of between about 0.5 and 0.2 micrometer, such that the filtrate comprising the compound of interest does not comprise any microorganism, or that the amount of microorganism in the filtrate is reduced to an acceptably low level.

The term "detergent-free" is herein preferably defined as that no detergent is added and/or used during an extraction step of any of the processes according to the invention; more preferably, no detergent is added and/or used at all during any of the processes according to the invention. If a detergent is used, e.g. as a processing aid in the form of an anti-foam agent, like the anti-foams from Sigma-Aldrich (cat. nr. A6426, A5633, A5757, A8011 or A5758), or molecules with comparable function from other manufacturers, during the cultivation of a population, this is considered to be within the scope of the process according to the invention. It is also possible that in a solution used within a process according to the present invention, small traces of a detergent are inherently present, e.g. traces of a detergent in a complex medium for cultivation; such inherent presence is also considered to be within the scope of the process according to the present invention.

A detergent is herein preferably defined as an agent, preferably a reagent, that has surfactant capacity and, when contacted with the bacterium, has the capacity to extract protein from the bacterium. A detergent can be an anionic, cationic, non-ionic (having a net charge of zero, also known as zwitterionic) or an ethyloxylate. Preferably, an antifoam agent, i.e. an agent that reduces and hinders the formation of foam in industrial process liquids such as the anti-foams from Sigma-Aldrich (cat. nr. A6426, A5633, A5757, A8011 or A5758) is not within the definition of a detergent. Cultivation of a population of a Gram negative bacterium in any of the processes according to the invention may be performed by any method known to the person skilled in the art. A preferred culture medium is a chemically defined medium, preferably such as described in Baart et al., 2007. The temperature may be varied at any temperature such as between about 30 and about 40° C. The pH may be varied at any pH such as at a pH from about 5.5 to 8.5. Preferred culture conditions comprise culturing at about 35° C. at pH 7.2 with aeration. Culture may be performed in several steps, including but not limited to a pre-culture or seed-culture and a main culture. The culture can be performed on any scale, including but not limited to shake flask cultivation, small-scale or large-scale cultivation (including continuous, batch, fed-batch, or solid state cultivation) in laboratory or industrial fermenters. Preferably, the volume of the culture is at least about 10 L, more preferably at least about 20 L, 40 L, 60 L 80 L, 100 L, 200 L, 300 L, 400 L, 500 L, 800 L, 1500 L, 5000 L, 10.000 L, 20.000 L or 40.000 L.

A population of a bacterium is herein defined as at least two bacteria, preferably of the same genus and species.

Preferably, the OMV are prepared from a Gram negative bacterium having a genetic modification which causes the bacterium to produce an LPS that is modified to have reduced toxicity. Preferably, the Gram negative bacterium has an LPS with reduced toxicity wherein the LPS (or its Lipid A moiety (LA)) is modified to have reduced toxicity. An LPS that is modified to have reduced toxicity is herein understood as an LPS that is modified to have less toxicity than the toxicity of a corresponding wild-type LPS. Preferably, the modified LPS has less than about 90, 80, 60, 40, 20, 10, 5, 2, 1, 0.5, or 0.2% of the toxicity of the corresponding wild-type LPS. The toxicities of wild-type and various modified LPS's with reduced toxicity may be determined in any suitable assay known in the art. A preferred assay for determining the toxicity, i.e. the biological activity of the LPS is the WEHI test for TNF-alpha induction in the MM6 macrophage cell line [Espevik and Niessen, 1986, J. Immunol. Methods 95: 99-105; Ziegler-Heitbrock et al., 1988, Int. J. Cancer 41: 456-461].

However, while it is preferred that the LPS of the Gram negative bacterium (or its LA moiety) has reduced toxicity, it is further preferred that the LPS retains at least part of immunostimulatory activity, i.e. adjuvant activity. Thus, the LPS with reduced toxicity of the Gram negative bacterium to be used in the invention preferably has at least about 10, 20, 40, 80, 90 or 100% of the immunostimulatory activity of the corresponding wild-type LPS, whereby the immunostimulatory activity is determined by measuring the production of at least one cytokine or the expression of at least one costimulatory molecule upon co-cultivation of dendritic cells (DC) with the Gram negative bacterium producing the LPS with reduced toxicity as described in Example 3 in WO 2005/107798. The cytokine produced by the DC is preferably selected from IL12, IL10, TNF-α, IL6 and IL-1β and the costimulatory molecule expressed by the DC is preferably selected from CD40 and CD86.

Gram negative LPS's having reduced toxicity of the Lipid A moiety but retaining (part of) the adjuvant activity, may e.g. be obtained from genetically modified Gram negative pathogens and as reviewed in WO02/09746. Genetically modified Gram negative pathogens producing LPS with reduced toxicity of the Lipid A moiety but retaining (part of) their adjuvant activity include e.g. Gram negative bacteria having one or more genetic modifications that decrease or knock-out expression of one or more genes selected from the lpxL1 and lpxL2 genes or homologues thereof (formerly known as htrB and msbB; see e.g. WO00/26384; U.S. Pat. No. 5,997,881) and the lipid A 4'-kinase encoding lpxK gene or a homologues thereof (see also below); and genetic modifications that effect the expression of one or more a heterologous lpxE and pagL genes. Preferred genetic modifications are modifications that decrease or knock-out expression of one or more genes selected from the lpxL1 and lpxL2 genes or homologues thereof. A preferred LPS with reduced toxicity of the Lipid A moiety but retaining (part of) its adjuvant activity is an LPS described in WO00/26384 and is an LPS with a lipid A having a reduced number of secondary acyl chains per molecule of LPS compared to the corresponding non-modified LPS molecule and having at least one secondary acyl chain bound to a primary acyl chain at the reducing end of the glucosamine disaccharide; preferably said lipid A has the same number of primary acyl chains as the non-modified LPS molecule and/or said lipid A has a secondary acyl chain on the primary acyl chain at the 2 position of the glucosamine at the reducing end of the glucosamine disaccharide and/or said LPS is an LPS wherein the secondary acyl chain is a lauroyl chain and/or said lipid A has a phosphoethanolamine attached to a phosphate group at the reducing end and/or said lipid A having the molecular structure:

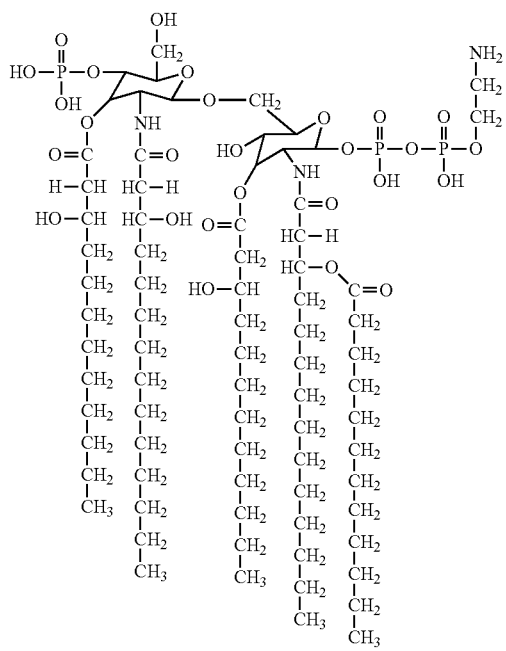 [SMILES: CCCCCCCCCCCC(=O)OC(CCCCCCCCCCC)CC(=O)NC1C(OP(=O)(O)OP(=O)(O)OCCN)OC(COC2OC(CO)C(OP(=O)(O)O)C(OC(=O)CC(O)CCCCCCCCC)C2NC(=O)CC(O)CCCCCCCCCCC)C(O)C1OC(=O)CC(O)CCCCCCCCC]

Stationary growth phase is herein defined as a phase in culture where the growth rate has slowed as a result of nutrient depletion and/or accumulation of toxic products. This phase is e.g. reached as the bacteria begin to exhaust specific nutrient resources that were previously available. The stationary growth phase is preferably a period in culture where the rate of bacterial growth is close or equal to the rate of bacterial death. Preferably, the growth rate of the bacteria has slowed to below 0.1. More preferably, the growth rate of the bacteria has changed from between about 0.3-0.5 to below 0.1, even more preferably from about $0.40\pm0.10$ h$^{-1}$ (exponential growth) to $0.00\pm0.10$ h$^{-1}$ (stationary growth). The onset of the stationary growth phase can be determined by the person skilled in the art by any means available, including but not limited to monitoring bacterial growth with timely measuring optical density or dry weight measurements, or by measuring depletion of nutrients such as carbon sources such as glucose, nitrogen sources such as amino acids or ammonium, or by monitoring oxygen consumption or $CO_2$ production Preferably, the onset of the stationary growth phase is defined by determining at least one of the maximum oxygen consumption rate and the maximum $CO_2$ production rate. Preferably therefore, at least one of the maximum oxygen consumption rate and the maximum $CO_2$ production rate are monitored continuously at least during the cultivation step.

The onset of stationary phase may be induced passively, such as in batch culture when a nutrient becomes depleted. The onset of stationary phase may be induced actively, such as by depletion of a nutrient from the feed in fed-batch culture, by pH change, or by stopping or reducing the feed or oxygen supply. After the onset of stationary phase, the bacteria are preferably maintained under the same culture conditions as present at the onset of stationary phase, such as temperature, oxygen concentration, stirring, pH etc. Preferably, after the time point at least 1 hour after the onset of stationary growth phase as specified earlier herein, the bacteria or the culture comprising the bacteria is cooled to a temperature of below about 20° C., more preferably below about 15° C., 10° C., 8° C., 6° C., more 5° C., 4° C., 3° C., 2° C., or below about 1° C. When cooled, the bacteria or the culture comprising the bacteria may be stored at the temperature below 20° C. as defined here above. The bacteria may be stored at below −20° C., more preferably at below −80° C., −135° C. or below −150° C.; however, preferably the bacteria or the culture comprising the bacteria is not cooled to a temperature that would cause freezing of (part of) the culture or bacteria, such as e.g. temperatures below 0° C. since this could induce lysis of the bacteria.

After the time point at least 1 hour after the onset of stationary growth phase as specified earlier herein, the bacteria obtained are incubated in a medium comprising a metal chelating agent, preferably EDTA, to extract OMV. The metal chelating agent may be any metal chelating agent known to the person skilled in the art. Preferably, the metal chelating agent is one or at least one selected from the group consisting of polyamino carboxylic acids e.g. nitrilotriacetic acid (NTA), diethylene triamine pentaacetic acid (DTPA), ethylene glycol tetraacetic acid (EGTA), 1,2-bis(o-aminophenoxy)ethane-N,N,N',N'-tetraacetic acid (BAPTA), ethylenediaminetetraacetic acid (EDTA) Preferably, the metal chelating agent is EDTA. The incubation can be performed at any scale. The invention encompasses that bacteria from several different cultures are incubated in a single medium comprising a metal chelating agent, preferably EDTA, to extract OMV. Preferably, the volume of the incubation is at least about 10 L, more preferably at least about 20 L, 40 L, 60 L 80 L, 100 L, 200 L, 300 L, 400 L, 500 L, 800 L, 1500 L, 5000 L, 10.000 L, 20.000 L or 40.000 L. The bacteria may contacted with the medium comprising a metal chelating agent, preferably EDTA, by any means knows to the person skilled in the art. The bacteria may e.g. be separated from the culture medium by centrifugation and then be contacted with the medium comprising a metal chelating agent, preferably EDTA, e.g. by resuspending in the medium comprising a metal chelating agent, preferably EDTA. Preferably, the culture medium is gradually replaced by the medium comprising a metal chelating agent, preferably EDTA. Preferably, the bacteria obtained in the culture are first concentrated by microfiltration. Preferably, the volume of the culture is decreased 2-fold, more preferably 3-fold, more preferably 4-fold, more preferably 5-fold, more preferably 6-fold, more preferably 7 fold, more preferably 9-fold, more preferably 10-fold. The concentrated bacterial suspension is then diafiltrated. Preferably the culture medium is gradually replaced with a buffer that has the appropriate pH for extraction. Diafiltration is herein defined as microfiltration with constant volume, wherein a first medium comprising a compound of interest is replaced through continuous dialysis with a second medium, such that the compound of interest after diafiltration is present in the second medium. As such, the medium of the culture medium is thus gradually replaced by another suitable medium, preferably 100 mM Tris-HCl pH 8.6. The concentration and diafiltration may be performed simultaneously or subsequently. When performed simultaneously, the second medium is a medium with the appropriate pH for extraction and comprising a metal chelating agent, preferably EDTA, or a medium buffer with the appropriate pH to which an appropriate amount of a metal chelating agent, preferably EDTA is added directly after diafiltration; preferably, the second medium comprises a buffering agent such as Tris-HCl, at a concentration of between about 10 mM to 250 mM, with a pH higher than about pH 7.5, preferably as defined below, to which between about 1 mM to 100 mM of a metal chelating agent, preferably EDTA is added. Diafiltration is preferably performed until the first medium has completely been replaced by the second medium; this process may take at least 1 hour-4 hours, or more. Diafiltration can be performed using any membrane suitable known to the person skilled in the art. Preferably, hollow fiber elements with pore size 0.2 micrometer are used.

The medium comprising a metal chelating agent, preferably EDTA, may be any medium suitable for the extraction of OMV. Preferably, the medium does not comprise a detergent. Preferably, the medium comprising a metal chelating agent, preferably EDTA, further comprises a buffering agent or a mixture of buffering agents; examples of buffering agents are, but are not limited to Tris and phosphate. A preferred medium is 100 mM Tris-HCl; pH 8.6 with 10 mM EDTA.

Preferably, the medium comprising a metal chelating agent, preferably EDTA, has a concentration of metal chelating agent, preferably EDTA of between about 1 and 100 mM. Preferably, the concentration is between about 1 and 50 mM, more preferably between about 1 and 25 mM, 2 and 25 mM, 3 and 25 mM, 4 and 25 mM, 5 and 25 mM, or 5 and 20 mM, and most preferably between about 5 and 15 mM such as about 5, 6, 7, 8, 9, 10, 11, 12, 13, 14 and 15 mM. Preferably, the metal chelating agent is one as defined earlier herein, more preferably, the metal chelating agent is EDTA. Preferably, the medium has the preferred value of the concentration of metal chelating agent, preferably EDTA, after the bacteria have been contacted with the medium. The concentration of metal chelating agent, preferably EDTA, of the medium may be adjusted. Adjustment may take place during any time of contacting the bacteria with the medium or during incubation of the bacteria in the medium, and may be performed more than once and may be performed continuously and/or automatically. The person skilled in the art knows how to adjust the metal chelating agent concentration of a medium, e.g. by measuring the metal chelating agent concentration and by adding an appropriate amount of metal chelating agent, either as a solid or as a solution. When the metal chelating agent is EDTA, the EDTA may be in any form, e.g. as acid or as one of the EDTA salts known to the person skilled in the art, or as mixture of several forms of EDTA.

Preferably, the medium comprising a metal chelating agent, preferably EDTA, has a pH higher than about pH 7.5. Preferably, the pH of the medium a metal chelating agent, preferably EDTA is higher than about pH 7.6, pH 7.7, pH 7.8, pH 7.9, pH 8.0, pH 8.1, pH 8.2, pH 8.3, pH 8.4, pH 8.5, pH 8.6, pH 8.7, pH 8.9, pH 9.0, pH 9.1, pH 9.2, pH 9.3, pH 9.4 or pH 9.5. More preferably, the pH of the medium is between about pH 7.5 and pH 9.5, more preferably between about pH 8.0 and pH 9.0, more preferably between about pH 8.2 and pH 8.8, more preferably between about pH 8.4 and pH 8.7. Most preferably, the pH of the medium comprising a metal chelating agent, preferably EDTA is about pH 8.6. Preferably the pH is at the preferred value after the bacteria have been contacted with the medium comprising a metal chelating agent, preferably EDTA. The pH of the medium a comprising metal chelating agent, preferably EDTA may be adjusted. Adjustment may take place during any time of contacting the bacteria with the medium or during incubation of the bacteria in the medium, and may be performed more than once and may be performed continuously and/or automatically. The person skilled in the art knows how to adjust pH of a medium, e.g. by measuring the pH and adding a suitable acid or base to the medium comprising a metal chelating agent, preferably EDTA.

A preferred medium for the extraction of the OMV is a medium with pH higher than about pH 7.5 and wherein the concentration of the metal chelating agent, preferably EDTA, is between about 5 to 15 mM; more preferably, the pH is about pH 8.6 and the concentration of the metal chelating agent, preferably EDTA, is between about 5 to 15 mM; preferably, the medium comprises Tris-HCl, e.g. 100 mM as a buffering agent.

After incubation of the bacteria in a medium comprising a metal chelating agent, preferably EDTA to extract the OMV, the OMV are recovered by at least removing the bacteria from the OMV. Removal of the bacteria from the OMV may be performed by any means known to the person skilled in the art. Examples of methods for removal are, but are not limited to: filtration with 0.5-0.2 µm pore size, centrifugation, or any other method for (spontaneous) sedimentation of bacteria. A preferred method to remove the bacteria from the OMV is by batch or continuous centrifugation, depending on the scale of the process, e.g. batch centrifugation for volumes up to about 100 L and continuous centrifugation for volumes above about 100 L.

After recovery or simultaneously with recovery, the OMV preparation may be purified. Purification may comprise any methods known to the person skilled in the art. Preferably at least one method from the following group is applied: ultrafiltration as described earlier herein and/or diafiltration to exchange the medium, e.g. to remove the metal chelating agent from the extraction medium and/or to concentrate the OMV preparation; degradation of nucleic acids such as deoxyribonucleic acid (DNA) and ribonucleic acid (RNA), which may be performed enzymatically using one or more suitable nucleases, preferably using Benzonase® (Merck, the Netherlands); clarification by filtration, preferably using a filter with a pore size of between about 0.5 µM and 1.0 µM; gel filtration (such as Size Exclusion Chromatography; Sepharose 6 Fast Flow column material; OMV are recovered from the void volume of the column); sterile filtration as described earlier herein. Preferably, at least sterile filtration is applied. Preferably, more than one purification method is applied. Preferably, the following methods are consecutively applied: ultrafiltration (e.g. 100 or 300 kDa cut-off), diafiltration (e.g. 100 or 300 kDa cut-off), enzymatic degradation of nucleic acids, clarification, gel filtration and sterile filtration, although not necessarily in this order. A preferred process according to the invention does not include ultracentrifugation.

Degradation of nucleic acids using benzonase is preferably performed in a buffer of pH 8.4+/−0.4, comprising between about 0.1 to 10 U benzonase/ml and between about 1 to 10 mM of $Mg^{2+}$, at 4° C. to 37° C. for 1 to 20 hours.

Preferably, in any of the processes according to the invention, the population of a Gram-negative bacterium comprises a species of *Neisseria, Bordetella, Haemophilus, Actinobacillus* or *Pasteurella*; more preferably a species of *Neisseria* or *Bordetella*; even more preferably, the population of a Gram-negative bacterium comprises a *Neisseria lactamica*, a *Neisseria gonorrheae*, a *Neisseria meningitidis*, a *Bordetella pertussis*, or a *Pasteurella multocida*; even more preferably a *Neisseria meningitidis*, preferably a serogroup B *Neisseria meningitidis* or a *Bordetella pertussis*.

Preferably, the population of a Gram-negative bacterium comprises a Gram-negative bacterium having one or more mutations to decrease or knock-out expression of a gene product. Preferably, the gene product is selected from the group consisting of Cps, CtrA, CtrB, CtrC, CtrD, ExbB, ExbD, FrpB, GalE, HtrB, MsbB, LpbB, LpxK, LpxL1, Nmb0033, OpA, OpC, RmpM, PhoP, PilC, PmrE, PmrF, PorA, PorB, SiaA, SiaB, SiaC, SiaD, SynA, SynB, SynC, TbpA and TbpB, or homologues thereof; many of these mutations are reviewed in WO02/09746. Preferably, the gene product is selected from the group consisting of Cps, lipid A biosynthesis gene products including LpxL1, RmpM, PorA, PorB and OpA. Preferably, the Gram-negative bacterium has at least mutations to decrease or knock-out expression of LpxL1, preferably such as described in WO00/26384. Preferably, the Gram-negative bacterium has at least mutations to decrease or knock-out expression of both LpxL1 and RmpM. Preferably, LpxL1 has at least about 30% sequence identity, more preferably at least about 35%, 40%, 45%, 50%, 55%, 60%, 65%, 70%, 75%, 80%, 85%, 90%, 95%, 96%, 97%, 98%, or 99% sequence identity with the amino acid sequence of SEQ ID NO: 1. Most preferably, LpxL1 is identical to the amino acid sequence of SEQ ID NO: 1.

Preferably, RpmM has at least about 30% sequence identity, more preferably at least about 35%, 40%, 45%, 50%, 55%, 60%, 65%, 70%, 75%, 80%, 85%, 90%, 95%, 96%, 97%, 98%, or 99% sequence identity with the amino acid sequence of SEQ ID NO: 2. Most preferably, RpmM is identical to the amino acid sequence of SEQ ID NO: 2.

Preferably, the Gram-negative bacterium is a *Neisseria meningitidis* strain that is a replicate or derivative of *Neisseria meningitidis* serogroup B isolate H44/76 [Holten et al, 1979; van den Dobbelsteen et al, 2007].

It is understood that replicates and/or derivatives of any strain according to the invention are encompassed by the invention. The term "replicate" refers to the biological material that represents a substantially unmodified copy of the material, such as material produced by growth of micro-organisms, e.g. growth of bacteria in culture media. The term "derivative" refers to material created from the biological material and which is substantially modified to have new properties, for example caused by heritable changes in the genetic material. These changes can either occur spontaneously or be the result of applied chemical and/or physical agents (e.g. mutagenesis agents) and/or by recombinant DNA techniques as known in the art. When referring to a strain "derived" from another strain, it is understood that both "replicates" of that strain, as well as "derivatives" of the strain are encompassed, as long as the derived strain can be used to elicit an immune response against the Gram negative bacterium used in the method of the invention, such as e.g. *Neisseria meningitidis*.

Percentage of identity is herein preferably determined by calculating the ratio of the number of identical nucleotides/amino acids in the sequence divided by the length of the total nucleotides/amino acids minus the lengths of any gaps. DNA multiple sequence alignment was herein performed using any suitable sequence alignment software package available to a person skilled in the art. The minimal length of a relevant amino acid sequence showing 30% or higher identity level should preferably be about 40 amino acids, more preferably about 50, 70, 100, 150, 170, 200, 210, 220, 230, 240 or more amino acids, and in case of lpxL1 more preferably about 50, 70, 100, 150, 170, 200, 210, 220, 230, 240, 250, 260, 270, 280, 290, 295 or more amino acids. Preferably, the sequence identity is calculated over the entire sequence of SEQ ID NO: 1 or 2.

Expression will herein be understood to include any step involved in the production of a polypeptide including, but not limited to transcription, post-transcriptional modification, translation, post-translational modification, and secretion.

To decrease or knock-out expression a gene product defined earlier herein, the person skilled in the art has a plethora of well-known tools available. It is routine practice for the person skilled in the art to choose an adequate strategy to introduce a suitable modification in a polynucleotide in order to decrease or knock-out expression of a functional gene product. For example, methods for in vitro mutagenesis are described in Sambrook et al. (Molecular cloning, A laboratory Manual, $2^{nd}$ ed., Cold Spring Harbor Laboratory Press, Cold Spring Harbor, N.Y., USA, 1989). Corresponding methods are also available commercially in the form of kits (e.g., Quikchange site-directed mutagenesis kit by Stratagene, La Jolla, USA). Deletion of a polynucleotide may, for example, be accomplished by the gene replacement technology that is well known to the skilled person.

Preferably, the population of a Gram-negative bacterium comprises multiple species of Gram-negative bacteria such that multiple serotypes of antigen are expressed and finally end up in the OMV preparation. More preferably, a species of Gram-negative bacteria expresses multiple serotypes of an antigen. When the population of bacteria comprises a *Neisseria meningitidis*, the population preferably comprises a *Neisseria meningitidis* expressing multiple serotypes of porA antigen; more preferably, the population of bacteria comprises multiple species of *Neisseria meningitidis*, each species expressing multiple serotypes of porA antigen. Preferably, the population of a Gram-negative bacterium comprises three trivalent PorA *Neisseria meningitidis* strains, expressing a total of 9 PorA subtypes [van der Ley et al, 1995; Claassen et al, 1996; van den Dobbelsteen et al, 2007].

The Gram-negative bacterium, which preferably is a *Neisseria meningitidis* strain that is a replicate or derivative of *Neisseria meningitidis* serogroup β isolate H44/76, may express an antigen foreign to said Gram-negative bacterium. OMV prepared according to the invention prepared from said Gram-negative bacterium will comprise said foreign antigen. As such, the OMV according to the invention can be used as a vehicle with adjuvant activity and can conveniently be used for the treatment diseases or conditions associated with said foreign antigen. The antigen foreign to the Gram-negative bacterium may be any antigen and may be one or at least one selected from the group consisting of NadA protein, heparin binding protein, Q fever surface antigen, a *Chlamydia* antigen, pertactin, pertussis toxin, 92 kDa antigen, fim2, fim3, dermonecrotic toxin, factor H binding protein, polysaccharides from *Neisseria meningitis* serogroup A, C, W135 or Y, *Chlamydia* surface antigen, diphtheria toxoid, attenuated or inactivated polio virus, tetanus toxiod, *Haemophilus influenzae* b polysaccharide or auto-antigens associated with diseases where an autoimmune response may be involved such as e.g. Alzheimers disease and tumor antigens.

The foreign antigen may be expressed by any means known to the person skilled in the art; preferably the foreign antigen is targeted to the OMV. Preferably, the foreign antigen or a part thereof is fused to or comprised in *Neisseria meningitidis* serogroup B porA or a part thereof.

Within the scope of the invention, it is possible to culture or otherwise provide several species of Gram-negative bacteria, each expressing a single or multiple antigen serotype and to extract OMV simultaneously from one or more pooled populations of said bacteria. It is also within the scope of the present invention to extract the OMV separately from populations of bacteria and then preferably pool the preparations of OMV. It is further within the scope of the invention that different species Gram-negative bacteria are cultivated together in a single, mixed population or separately in individual populations or even in a combination of individual and mixed populations.

The OMV preparation obtained by any of the processes according to the present invention can conveniently be stored for future use, either in lyophilized form or in solution, or frozen in solution. In any of the processes according to the present invention, one or several compounds may be added to the OMV preparation such as a (colloidal) stabilizer, such as sucrose, in order to prevent aggregation and/or a preservative such as thiomersal in order to prevent microbial growth.

The OMV preparation obtained by any of the processes according to the present invention can conveniently be used for the preparation of a medicament, preferably a medicament for the treatment of meningitis, preferably said medicament is a vaccine against *Neisseria meningitidis* infection. Accordingly, any of the processes according to the present invention, may further comprise the step of combining the OMV with a pharmaceutically accepted excipient, such as a carrier, an adjuvant, a stabilizing agent, an osmotic agent, a buffering agent and/or a dispersing agent. In addition, in any of the processes according to the present invention, the OMV may be combined with a another antigen to prepare a mixed vaccine, preferably with antigens comprising outer membrane proteins from *Neisseria meningitis* serogroup B or from other gram-negative pathogens, including but nor limited to NadA protein, heparin binding protein, Q fever surface antigen, pertactin, pertussis toxin, 92 kDa antigen, fim2, fim3, dermonecrotic toxin, factor H binding protein, polysaccharides from *Neisseria meningitis* serogroup A, C, W135 or Y preferably conjugated to a suitable pharmaceutically accepted carrier protein, *Chlamydia* surface antigen, diphtheria toxoid, attenuated or inactivated polio virus, tetanus toxiod, *Haemophilus influenzae* b polysaccharide, preferably conjugated to a suitable pharmaceutically accepted carrier protein.

Vaccination is applied for the prophylactic protection against pathogens or for the treatment of diseases following pathogenic infection.

Adjuvants are herein defined to include any substance or compound that, when used in combination with an antigen, to immunize a subject, preferably a mammal, preferably a human, stimulates the immune system, thereby provoking, enhancing or facilitating the immune response against the antigen, preferably without generating a specific immune response to the adjuvant itself. Preferred adjuvants enhance the immune response against a given antigen by at least a factor of 1.5, 2, 2.5, 5, 10 or 20, as compared to the immune response generated against the antigen under the same conditions but in the absence of the adjuvant. Tests for determining the statistical average enhancement of the immune response against a given antigen as produced by an adjuvant in a group of animals or humans over a corresponding control group are available in the art. The adjuvant preferably is capable of enhancing the immune response against at least two different antigens.

The pharmaceutical carrier can be any compatible, non-toxic substance suitable to deliver the active ingredients, to the subject. Pharmaceutically acceptable carriers for intranasal delivery are exemplified by water, buffered saline solutions, glycerin, polysorbate 20, cremophor EL, and an aqueous mixture of caprylic/capric glyceride, and may be buffered to provide a neutral pH environment. Pharmaceutically acceptable carriers for parenteral delivery are exemplified by sterile buffered 0.9% NaCl or 5% glucose optionally supplemented with a 20% albumin. Preparations for parental administration must be sterile. The parental route for administration of the active ingredients is in accord with known methods, e.g. injection or infusion by subcutaneous, intravenous, intraperitoneal, intramuscular, intraarterial or intralesional routes. The compositions according to the invention are preferably administered by bolus injection. For oral administration, the active ingredient can be administered in liquid dosage forms, such as elixirs, syrups, and suspensions. Liquid dosage forms for oral administration can contain coloring and flavoring to increase patient acceptance. Methods for preparing parenterally, orally or intranasally administrable compositions are well known in the art and described in more detail in various sources, including, for example, Remington's Pharmaceutical Science (15th ed., Mack Publishing, Easton, Pa., 1980) (incorporated by reference in its entirety for all purposes).

In a second aspect, the present invention provides OMV obtainable by any one of the processes according to first aspect of the present invention. Preferably, said OMV is the directly derived product of any one of the processes according to the first aspect of the present invention.

The OMV preparation obtainable by any of the processes according to the present invention can conveniently be used for the preparation of a medicament, preferably a medicament for the treatment of meningitis, preferably said medicament is a vaccine against *Neisseria meningitidis* infection. Preferably, said OMV preparation is the directly derived product of any one of the processes according to the first aspect of the present invention. Accordingly, the present invention provides a pharmaceutical composition comprising OMV obtainable by any of the processes according to the present invention and pharmaceutically acceptable excipient, such as a carrier, an adjuvant, a stabilizing agent, an osmotic agent, a buffering agent and/or a dispersing agent, as described earlier herein. Preferably, said OMV is the directly derived product of any one of the processes according to the first aspect of the present invention. Since the present invention provides for OMV comprising adjuvant activity itself, a preferred pharmaceutical composition does not comprise an additional adjuvant other than the OMV comprising adjuvant activity.

The pharmaceutical composition may be used as a vaccine. The vaccine may be used for immunization (raising an immune response) or vaccination of a subject, preferably a mammal, preferably a human. In the pharmaceutical composition, the OMV may be combined with another antigen to prepare a mixed vaccine. i.e. in combination with vaccines against *Neisseria meningitidis* serogroup A, C, W135, Y, pneumococcal disease, diphtheria, whooping cough, polio, RSV, or tetanus The present invention further provides an OMV obtainable by any of the processes according to the present invention for use as a medicament, preferably in the treatment of meningitis. Preferably, said medicament is a vaccine against *Neisseria meningitidis* infection. Preferably, said OMV is the directly derived product of any one of the processes according to the first aspect of the present invention.

The present invention further provides the use of an OMV obtainable by any of the processes according to the present invention for the preparation of a medicament, preferably for the treatment of meningitis. Preferably, said medicament is a vaccine against *Neisseria meningitidis* infection. Preferably, said OMV is the directly derived product of any one of the processes according to the first aspect of the present invention.

The present invention further provides a process for eliciting in a subject an immune reaction, preferably against *Neisseria meningitidis*, comprising administering to said subject OMV obtainable by any of the processes according to the present invention or administering to said subject a pharmaceutical composition according to the invention, preferably a vaccine against *Neisseria meningitidis* infection. Preferably, said OMV is the directly derived product of any one of the processes according to the first aspect of the present invention.

The present invention further provides the use of the OMV according to the invention or a pharmaceutical composition according to the invention for eliciting in a subject an immune reaction, preferably against *Neisseria meningitidis*, comprising administering to said subject OMV according to the invention or a pharmaceutical composition according to the invention.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the gene present in Neisseria meningitidis serogroup β isolate H44/76 containing the nucleic acid sequence coding for the polypeptide should prevail.

All patent and literature references cited in the present specification are hereby incorporated by reference in their entirety.

The present invention is further described by the following example which should not be construed as limiting the scope of the invention.

Unless stated otherwise, the practice of the invention will employ standard conventional methods of molecular biology, virology, microbiology or biochemistry. Such techniques are described in Sambrook et al. (1989) Molecular Cloning, A Laboratory Manual (2$^{nd}$ edition), Cold Spring Harbor Laboratory, Cold Spring Harbor Laboratory Press; in Sambrook and Russell (2001) *Molecular Cloning: A Laboratory Manual*, Third Edition, Cold Spring Harbor Laboratory Press, NY; in Volumes 1 and 2 of Ausubel et al. (1994) Current Protocols in *Molecular Biology, Current Protocols*, USA; and in Volumes I and II of Brown (1998) *Molecular Biology LabFax*, Second Edition, Academic Press (UK); *Oligonucleotide Synthesis* (N. Gait editor); *Nucleic Acid Hybridization* (Hames and Higgins, eds.).

SEQUENCES

TABLE 1

Figure 1:
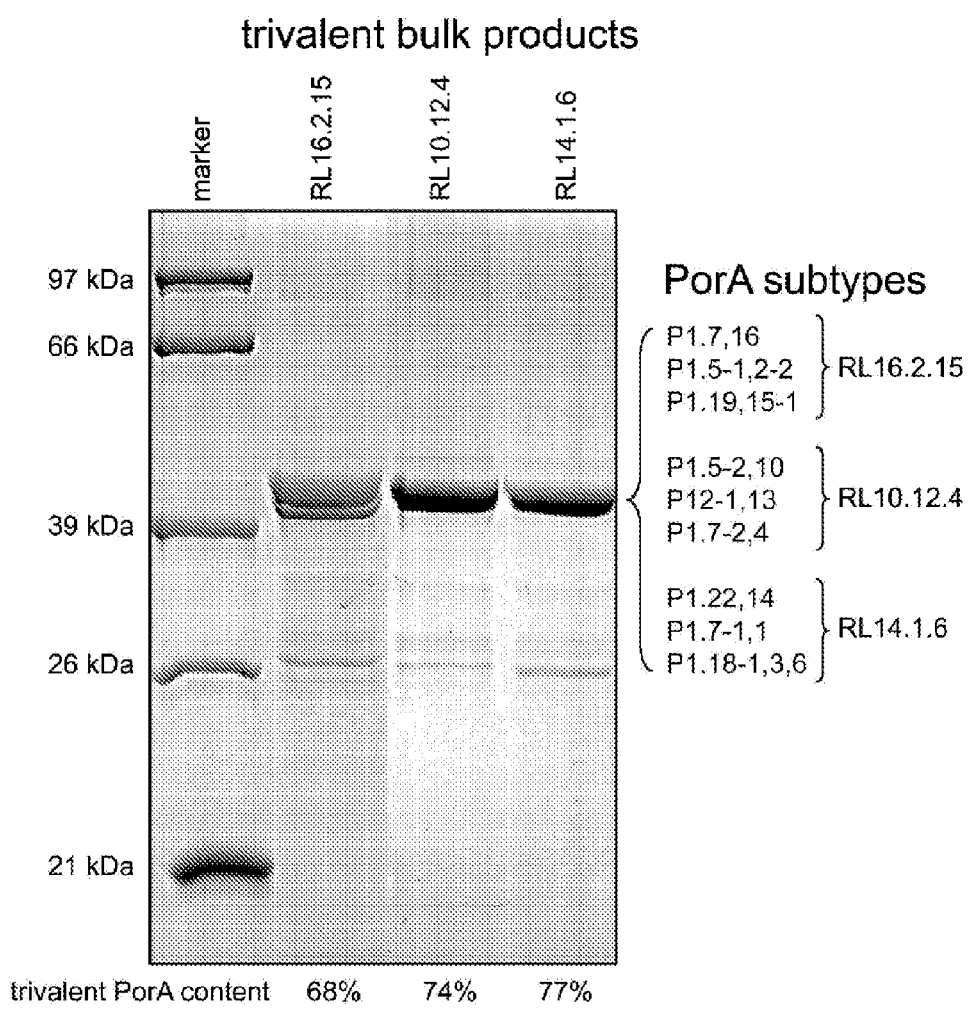
FIG. 1. Typical PorA content of trivalent bulk OMV from the three different trivalent RL NonaMen strains, together expressing the same 9 PorA subtypes as the HP NonaMen strains [van den Dobbelsteen et al, 2007], but with additional deletions in rmpM and lpxL1 genes. Depicted are trivalent bulk OMV from strains RL16215, RL10124 and RL1416, respectively, containing the PorA at approximately 41 kDa. Typical PorA content of RL NonaMen trivalent bulk OMV is between 60-80% of total protein content.

Sequences as set forth in the Sequence Listing

| SEQ ID NO: | SEQ type | Gene product |
|---|---|---|
| 1 | Polypeptide | *Neisseria meningitidis* lpxL1 |
| 2 | Polypeptide | *Neisseria meningitidis* rpmM |

EXAMPLES

Example 1

Scalable Manufacturing of Nonavalent OMV Vaccine Against *Neisseria meningitidis* Serotype B with Improved Yield and Purity The example below was performed with 40 L production culture, but is fully scalable to at least 800 L.

Three different *Neisseria meningitidis* serogroup B strains, originating from strain H44/76 [Fredriksen et al 1991] with additional deletions in cps, porB, rmpM and lpxL1 genes [Van de Waterbeemd et al 2010] and each expressing 3 unique PorA subtypes [Van den Dobbelsteen et al 2007], namely: P1.7,16/P1.5-1,2-2/P1.19,15-1 for strain RL16.2.15; P1.5-2,10/P12-1,13/P1.7-2,4 for strain RL10.12.4 and P1.22,14/P1.7-1,1/P1.18-1,3,6 for strain RL14.1.6, were stored at −135° C. as master seed lots. Master seed lots were thawed and expanded in shake flasks with 150 mL chemically defined medium [Baart et al 2007], divided in aliquots during exponential growth and stored at −135° C. after addition of glycerol to obtain working seed lots.

A primary preculture shake flask with chemically defined growth medium (Baart et al., 2007) was inoculated with a frozen working seed lot to provide an identical starting point for each production batch. During exponential growth the entire primary preculture was used to inoculate a secondary preculture, grown in 3 L chemically defined growth medium [Baart et al., 2007] in a bioreactor. During growth of the secondary preculture, temperature was controlled at 35° C. and dissolved oxygen concentration was controlled at 30% with variable stirring speed and addition of pure oxygen to the headspace airflow. During exponential growth, 1 L of biomass from the secondary preculture was transferred to 40 L chemically defined growth medium (Baart et al., 2007). The production culture was grown in a bioreactor with controlled temperature at 35° C., controlled pH at 7.2 with phosphoric acid and an anti-foam agent. Dissolved oxygen concentration was controlled at 30% with a combination of variable stirring speed and variable sparger airflow.

Stationary growth phase set in as determined by periodical OD measurement. The complete 40 L production culture was subsequently harvested by transferring into a stirred tank after 3 hours of stationary growth, to ensure an optimal balance between OMV yield and DNA release caused by bacterial lysis. The harvested production culture was first cooled to 20° C. and the volume was then reduced from 40 L to 6 L, using microfiltration with hollow fiber units (0.2 μm pore size). The concentrated harvest was diafiltrated with 2 volumes (12 L) 100 mM Tris-HCl buffer at pH 8.6 to adjust biomass pH to pH 8.4±0.4 Concentrated 100 mM EDTA solution was added to a final concentration of 10 mM to initiate OMV extraction followed by incubation for 30 min. at 20° C. in a stirred a tank at 100 rpm. Biomass was separated from the OMV extract with parallel batch centrifugation at semi-high-speed (6 buckets of 1 L; 30 min; 4° C.; 20.000×g); supernatant was retained. Batch centrifugation can be replaced with continuous centrifugation, if desired, for production at industrial scale. Supernatants were pooled and any residual pathogens or other particles were removed by depth filtration through a unit with a pore size narrowing from initially 0.5 µm to a final pore size of 0.2 µm.

The pathogen-free OMV extract was either stored at 4° C. for several weeks or was used directly for downstream processing. Volume was first reduced 12-fold to 0.5 L using ultrafiltration with 100 kDa cut-off and then diafiltrated with 2 volumes (1 L) 100 mM Tris-HCl buffer pH 8.6 to remove EDTA. Any genomic DNA present in the crude OMV was digested into fragments of less than 1000 bp using 1000 U/L (final concentration) Benzonase (Merck) in the presence of $Mg^{2+}$ cofactor (incubation at 21° C. for 18 hours). Any precipitates that may have formed during the Benzonase treatment were removed with a clarification filter (1.2-0.5 µm), before purifying the crude OMV on a gel filtration column that was packed with Sepharose 6 Fast Flow material (GE Healthcare) to remove DNA and small molecules from the OMV and allow a buffer change to storage buffer (10 mM Tris-HCl pH 7.4 with 3% (w/v) sucrose). Trivalent bulk OMV was then sterilized by filtration through a unit with 0.2 µm pore size and diluted to 1 mg/mL trivalent PorA with storage buffer (10 mM Tris-HCl pH 7.4 and 3% (w/v) sucrose). At this concentration, the bulk OMV could be safely stored at 4° C. for at least 6 months without loss of quality (Table 2).

Figure 2:
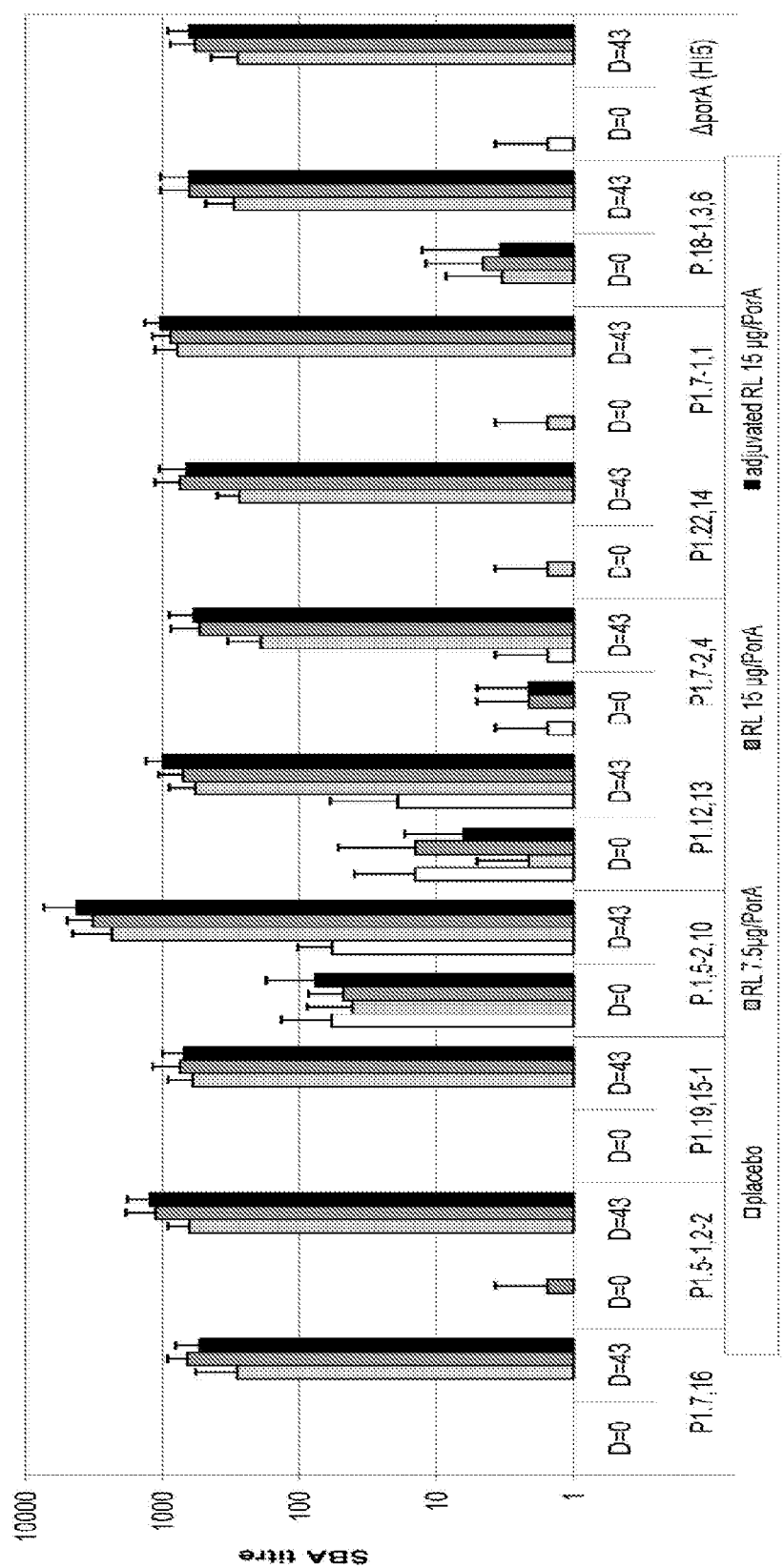
FIG. 2. Functional immunogenicity in rabbits of RL Nona-Men vaccines at 2 different doses (7.5 and 15 ng/PorA), with and without AlPO4 adjuvant. Pre-immunisation sera were taken at D=0 and post-immunisation sera were taken after three immunisations. All three vaccines gave significantly higher bactericidal titres at D=43 than at D=0, but no significant dose or adjuvant related effects were observed. This indicated that RL 7.5 μg/PorA contains sufficient antigen and that there is no need for the use of adjuvants when the vaccine is made with the process described herein.

The yield improvement obtained by harvesting the production culture at 3 hours after onset of stationary growth phase and performing the OMV extraction at pH 8.6 was 2.7-fold and could even be increased to 6.3-fold (Table 3), if harvest was delayed until 9 hours after onset of stationary growth and process modifications for improved DNA removal capacity were implemented (i.e. by using 10000 U/L Benzonase; The overall yield of the process described above was 30±4 mg trivalent PorA per liter production culture (the equivalent of 1338 human doses of 7.5 µg per PorA subtype). This PorA yield was obtained with an overall downstream process efficiency of 33±7%. Sterile filtration was included in this calculation and it is emphasized that the described process results in high filtration efficiency and reproducibility (92%±4%, Table 4) when compared to reference processes. The reference processes either used a preservative [thiomersalate; Fredriksen et al 1991 and Claasen et al 1996] to prevent yield loss associated with sterile filtration, or included process steps with mechanic shearing to reduce OMV size and improve efficiency [RWM 2007 NonaMen: Van den Dobbelsteen et al 2007 and Zollinger et al 2010]. In addition, trivalent bulk OMV from the strains mentioned above had improved PorA purity compared to OMV from other strains and processes [Zollinger et al 2010, U.S. Pat. No. 6,558,677 (FIG. 5); Fredriksen et al 1991]. Typical trivalent PorA content was 60-80% of total protein content (FIG. 2). Despite the high LPS content, low toxicity was observed. This was enabled by the lpxL1 deletion which attenuates LPS toxicity [Van de Waterbeemd et al 2010].

Trivalent bulk OMV from three strains listed previously was mixed proportionally to create nonavalent bulk OMV and consecutively diluted with storage buffer to a final concentration of 0.135 mg/mL nonavalent PorA (7.5 µg per PorA subtype per dose; no adjuvant) and 0.270 mg/mL nonavalent PorA (15 µg per PorA subtype per dose; both with and without $AlPO_4$ adjuvant). The three different vaccines were subdivided in 0.5 mL aliquots and stored at 4° C. until parenteral administration in rabbits on day 1, 15 and 29.

All OMV vaccines gave significantly higher bactericidal titres at D=43 than at D=0, but no significant dose or adjuvant related effects were observed. This indicated that RL 7.5 µg/PorA contained sufficient antigen and that there is no need for the use of adjuvants when the vaccine is made with the process according to the present invention. In addition the OMV vaccines induced cross-protection based on other antigens than PorA alone, as indicated by the high bactericidal titres against AporA strain HI5 (FIG. 2).

TABLE 2

Analysis of the different trivalent OMV during long-term storage.

| Analysis | unit | RL16215 trivalent bulk product | | | RL10124 trivalent bulk product | | | RL1416 trivalent bulk product | | |
| --- | --- | --- | --- | --- | --- | --- | --- | --- | --- | --- |
| | | t = 0 | t = 6 months | t = 12 months | t = 0 | t = 6 months | t = 12 months | t = 0 | t = 6 months | t = 12 months |
| total protein concentration | mg/mL | 1.31 | 1.26 | 1.27 | 1.16 | 1.09 | 1.07 | 1.68 | 1.88 | 1.6 |
| PorA percentage | % of total protein | 70 | 62 | 72 | 65 | 79 | 82 | 65 | 64 | 66 |
| percentage aggregation | % | 1.2 | 3.7 | 1.0 | 2.4 | 0.0 | 0.0 | 7.0 | 2.0 | 0.0 |
| particle diameter | d · nm | 79 | 77 | 80 | 70 | 70 | 71 | 67 | 81 | 77 |

TABLE 3

OMV and DNA yields obtained with different setpoints for harvest (in hours after onset of stationary growth) and pH (of the EDTA extraction buffer). Results were calculated with predictive models, obtained from the outcome of an experimental design study. In results #1 to #3, harvest and pH setpoints were optimized for the lowest (#1) or highest (#2) possible OMV yield and for the highest OMV yield with a restriction on DNA yield (#3). Results #4 to #8 were obtained with predefined setpoints for harvest and a fixed pH setpoint. Yield is defined in mg/L crude OMV extract.

| | optimization target | | setpoint | | results | | | |
| --- | --- | --- | --- | --- | --- | --- | --- | --- |
| | OMV yield | DNA yield | harvest | pH | OMV yield | DNA yield | OMV yield relative to #1 | remarks |
| #1 | Minimize | — | 1.0 | 7.4 | 35 ± 17 | 11 ± 8 | — | lowest possible OMV yield, no restriction on DNA yield |

TABLE 3-continued

OMV and DNA yields obtained with different setpoints for harvest (in hours after onset of stationary growth) and pH (of the EDTA extraction buffer). Results were calculated with predictive models, obtained from the outcome of an experimental design study. In results #1 to #3, harvest and pH setpoints were optimized for the lowest (#1) or highest (#2) possible OMV yield and for the highest OMV yield with a restriction on DNA yield (#3). Results #4 to #8 were obtained with predefined setpoints for harvest and a fixed pH setpoint. Yield is defined in mg/L crude OMV extract.

| | optimization target | | setpoint | | results | | | |
|---|---|---|---|---|---|---|---|---|
| | OMV yield | DNA yield | harvest | pH | OMV yield | DNA yield | OMV yield relative to #1 | remarks |
| #2 | Maximize | — | 9.0 | 9.0 | 227 ± 17 | 80 ± 9 | 6.5-fold | highest possible OMV yield, no restriction on DNA yield |
| #3 | Maximize | 0 µg | 3.3 | 8.4 | 99 ± 11 | 0 ± 10 | 2.8-fold | highest possible OMV yield while maintaining a low DNA yield |
| #4 | — | — | 1.0 | 8.6 | 54 ± 15 | 7 ± 7 | 1.5-fold | predefined setpoints; no yield targets specified |
| #5 | — | — | 3.0 | 8.6 | 95 ± 12 | −2 ± 10 | 2.7-fold | |
| #6 | — | — | 5.0 | 8.6 | 137 ± 11 | 9 ± 12 | 3.9-fold | |
| #7 | — | — | 7.0 | 8.6 | 179 ± 12 | 39 ± 10 | 5.1-fold | |
| #8 | — | — | 9.0 | 8.6 | 221 ± 15 | 90 ± 7 | 6.3-fold | |

TABLE 4

Sterile filtration efficiency of three consecutive bulk OMV batches. Minor losses were observed (<10%), which were mainly caused by the dead volume of the sterile filter.

| measurement | batch 1 | batch 2 | batch 3 | average |
|---|---|---|---|---|
| trivalent PorA yield before sterile filtration (mg) | 1553 | 1404 | 1308 | 1422 ± 124 |
| trivalent PorA yield after sterile filtration (mg) | 1420 | 1229 | 1257 | 1302 ± 103 |
| efficiency sterile filtration (%) | 91% | 88% | 96% | 92 ± 4% |

LIST OF REFERENCES

1. Girard M P, Preziosi M P, Aguado M T, Kieny M P. A review of vaccine research and development: meningococcal disease. Vaccine 2006; 24(22):4692-700.
2. Sharip A, Sorvillo F, Redelings M D, Mascola L, Wise M, Nguyen D M. Population based analysis of meningococcal disease mortality in the United States: 1990-2002. Pediatr Infect Dis J 2006; 25(3):191-4.
3. Kaplan S L, Schutze G E, Leake J A, Barson W J, Halasa N B, Byington C L, et al. Multicenter surveillance of invasive meningococcal infections in children. Pediatrics 2006; 118 (4):e979-84.
4. Trotter C L, Chandra M, Cano R, Larrauri A, Ramsay M E, Brehony C, et al. A surveillance network for meningococcal disease in Europe. FEMS Microbiol Rev 2007; 31(1): 27-36.
5. Gray S J, Trotter C L, Ramsay M E, Guiver M, Fox A J, Borrow R, et al. Epidemiology of meningococcal disease in England and Wales 1993/94 to 2003/04: contribution and experiences of the Meningococcal Reference Unit. J Med Microbiol 2006; 55(Pt 7):887-96.
6. Snape M D, Perrett K P, Ford K J, John T M, Pace D, Yu L M, et al Immunogenicity of a tetravalent meningococcal glycoconjugate vaccine in infants: a randomized controlled trial. Jama 2008; 299(2):173-84.
7. Morley S L, Pollard A J. Vaccine prevention of meningococcal disease, coming soon? Vaccine 2001; 20(5-6):666-87.
8. Finne J, Leinonen M, Makela P H. Antigenic similarities between brain components and bacteria causing meningitis. Implications for vaccine development and pathogenesis. Lancet 1983; 2(8346):355-7.
9. Bjune G, Hoiby E A, Gronnesby J K, Arnesen O, Fredriksen J H, Halstensen A, et al. Effect of outer membrane vesicle vaccine against group B meningococcal disease in Norway. Lancet 1991; 338(8775): 1093-6.
10. Thornton V, Lennon D, Rasanathan K, O'Hallahan J, Oster P, Stewart J, et al. Safety and immunogenicity of New Zealand strain meningococcal serogroup B OMV vaccine in healthy adults: beginning of epidemic control. Vaccine 2006; 24(9):1395-400.
11. Martin D R, Walker S J, Baker M G, Lennon D R. New Zealand epidemic of meningococcal disease identified by a strain with phenotype B:4:P1.4. J Infect Dis 1998; 177(2): 497-500.
12. Sierra G V, Campa H C, Varcacel N M, Garcia I L, Izquierdo P L, Sotolongo P F, et al. Vaccine against group B Neisseria meningitidis: protection trial and mass vaccination results in Cuba. NIPH Ann 1991; 14(2):195-207, discussion 208-10.
13. Fredriksen J H, Rosenqvist E, Wedege E, Bryn K, Bjune G, Froholm L O, et al. Production, characterization an control of MenB-vaccine "Folkehelsa": an outer membrane vesicle vaccine against group B meningococcal disease. NIPH Ann 1991; 14(2):67-79, discussion 79-80.
14. Deatherage B L, Lara J C, Bergsbaken T, Rassoulian Barrett S L, Lara S, Cookson B T. Biogenesis of bacterial membrane vesicles. Mol Microbiol 2009; 72(6):1395-407.
15. Saukkonen K, Leinonen M, Abdillahi H, Poolman J T. Comparative evaluation of potential components for group B meningococcal vaccine by passive protection in the infant rat and in vitro bactericidal assay. Vaccine 1989; 7(4): 325-8.
16. Martin D R, Ruijne N, McCallum L, O'Hallahan J, Oster P. The VR2 epitope on the PorA P1.7-2,4 protein is the major target for the immune response elicited by the strain-specific group B meningococcal vaccine MeNZB. Clin Vaccine Immunol 2006; 13(4):486-91.
17. van der Ley P, van der Biezen J, Poolman J T. Construction of Neisseria meningitidis strains carrying multiple chromosomal copies of the porA gene for use in the production of a multivalent outer membrane vesicle vaccine. Vaccine 1995; 13(4):401-7.

18. Claassen I, Meylis J, van der Ley P, Peeters C, Brons H, Robert J, et al. Production, characterization and control of a *Neisseria meningitidis* hexavalent class 1 outer membrane protein containing vesicle vaccine. Vaccine 1996; 14(10):1001-8.
19. de Kleijn E, van Eijndhoven L, Vermont C, Kuipers B, van Dijken H, Rumke H, et al. Serum bactericidal activity and isotype distribution of antibodies in toddlers and schoolchildren after vaccination with RIVM hexavalent PorA vesicle vaccine. Vaccine 2001; 20(3-4):352-8.
20. van den Dobbelsteen G P, van Dijken H H, Pillai S, van Alphen L Immunogenicity of a combination vaccine containing pneumococcal conjugates and meningococcal PorA OMVs. Vaccine 2007; 25(13):2491-6.
21. Arigita C, Luijkx T, Jiskoot W, Poelen M, Hennink W E, Crommelin D J, et al. Welldefined and potent liposomal meningococcal B vaccines adjuvated with LPS derivatives. Vaccine 2005; 23(43):5091-8.
22. Arigita C, Kersten G F, Hazendonk T, Hennink W E, Crommelin D J, Jiskoot W. Restored functional immunogenicity of purified meningococcal PorA by incorporation into liposomes. Vaccine 2003; 21(9-10):950-60.
23. Steeghs L, Tommassen J, Leusen J H, van de Winkel J G, van der Ley P. Teasing apart structural determinants of 'toxicity' and 'adjuvanticity': implications for meningococcal vaccine development. J Endotoxin Res 2004; 10(2): 113-9.
24. Koeberling O, Giuntini S, Seubert A, Granoff D M. Meningococcal outer membrane vesicle vaccines derived from mutant strains engineered to express factor H binding proteins from antigenic variant groups 1 and 2. Clin Vaccine Immunol 2009; 16(2):156-62.
25. Koeberling O, Seubert A, Granoff D M. Bactericidal antibody responses elicited by a meningococcal outer membrane vesicle vaccine with overexpressed factor H-binding protein and genetically attenuated endotoxin. J Infect Dis 2008; 198(2):262-70.
26. van der Voort E R, van der Ley P, van der Biezen J, George S, Tunnela O, van Dijken H, et al. Specificity of human bactericidal antibodies against PorA P1.7,16 induced with a hexavalent meningococcal outer membrane vesicle vaccine. Infect Immun 1996; 64(7):2745-51.
27. Hoist J, Martin D, Arnold R, Huergo C C, Oster P, O'Hallahan J, et al. Properties and clinical performance of vaccines containing outer membrane vesicles from *Neisseria meningitidis*. Vaccine 2009; 27(Suppl. 2):B3-12.
28. Cametti C. Polyion-induced aggregation of oppositely charged liposomes and charged colloidal particles: the many facets of complex formation in low density colloidal systems. Chem Phys Lipids 2008; 155(2):63-73.
29. Zollinger W D, Mandrell R E, Griffiss J M, Altieri P, Berman S. Complex of meningococcal group B polysaccharide and type 2 outer membrane protein immunogenic in man. J Clin Invest 1979; 63(5):836-48.
30. Post D M, Zhang D, Eastvold J S, Teghanemt A, Gibson B W, Weiss J P. Biochemical and functional characterization of membrane blebs purified from *Neisseria meningitidis* serogroup B. J Biol Chem 2005; 280(46):38383-94.
31. Devoe I W, Gilchrist J E. Release of endotoxin in the form of cell wall blebs during in vitro growth of *Neisseria meningitidis*. J Exp Med 1973; 138(5):1156-67.
32. Hoekstra D, van der Laan J W, de Leij L, Witholt B. Release of outer membrane fragments from normally growing *Escherichia coli*. Biochim Biophys Acta 1976; 455(3):889-99.
33. Guthrie T, Wong S Y, Liang B, Hyland L, Hou S, Hoiby E A, et al. Local and systemic antibody responses in mice immunized intranasally with native and detergent extracted outer membrane vesicles from *Neisseria meningitidis*. Infect Immun 2004; 72(5):2528-37.
34. Katial R K, Brandt B L, Moran E E, Marks S, Agnello V, Zollinger W D. Immunogenicity and safety testing of a group B intranasal meningococcal native outer membrane vesicle vaccine. Infect Immun 2002; 70(2):702-7.
35. Saunders N B, Shoemaker D R, Brandt B L, Moran E E, Larsen T, Zollinger W D. Immunogenicity of intranasally administered meningococcal native outer membrane vesicles in mice. Infect Immun 1999; 67(1):113-9.
36. Drabick J J, Brandt B L, Moran E E, Saunders N B, Shoemaker D R, Zollinger W D. Safety and immunogenicity testing of an intranasal group B meningococcal native outer membrane vesicle vaccine in healthy volunteers. Vaccine 1999; 18(1-2):160-72.
37. Ferrari G, Garaguso I, Adu-Bobie J, Doro F, Taddei A R, Biolchi A, et al. Outer membrane vesicles from group B *Neisseria meningitidis* delta gna33 mutant: proteomic and immunological comparison with detergent-derived outer-membrane vesicles. Proteomics 2006; 6(6):1856-66.
38. van der Ley P, Steeghs L, Hamstra H J, ten Hove J, Zomer B, van Alphen L.
Modification of lipid A biosynthesis in *Neisseria meningitidis lpxL* mutants: influence on lipopolysaccharide structure, toxicity, and adjuvant activity. Infect Immun 2001; 69(10): 5981-90.
39. Fisseha M, Chen P, Brandt B, Kijek T, Moran E, Zollinger W. Characterization of native outer membrane vesicles from lpxL mutant strains of *Neisseria meningitides* for use in parenteral vaccination. Infect Immun 2005; 73(7):4070-80.
40. Van de Waterbeemd B, Streefland M, van der Ley P, Zomer B, van Dijken H, Martens D, Wijffels R, van der Pol L. Improved OMV vaccine against *Neisseria meningitidis* using gentically engineered strains and detergent-free purification process. Vaccine 2010; 28: 4810-4816.
41. Prachayasittikul, Z et al. EDTA-induced membrane fluidization and destabilization: biophysical studies on artificial lipid membranes. Acta Biochim Biophys Sin 2007; 39(11): 901-913.
42. Holten, E., Serotypes of *Neisseria meningitidis* isolated from patients in Norway during the first six months of 1978. J Clin Microbiol, 1979. 9(2): p. 186-188.
43. Baart, G. J., et al., Scale-up for bulk production of vaccine against meningococcal disease. Vaccine, 2007. 25(34): p. 6399-408.

The invention claimed is:

1. A process for producing a detergent-free preparation of bacterial outer membrane vesicles (OMV) for use in vaccines, said process comprising the steps of:
   (a) cultivating a population of Gram-negative bacteria in culture to stationary growth phase;
   (b) beginning at a time at least about 1 hour after onset of the stationary growth phase, incubating the bacteria obtained in step (a) in a medium adjusted to, or having a pH higher than, pH 8.0 and a concentration of a metal chelating agent of between about 1 and 100 mM to extract said bacterial OMV; and
   (c) after step (b), recovering the extracted bacterial OMV by separation of the bacterial OMV from the bacteria.

2. The process according to claim 1, wherein the Gram-negative bacteria comprise a genetic modification which causes the bacteria to produce a lipopolysaccharide (LPS) with reduced toxicity compared to a corresponding wild-type LPS while retaining at least part of the LPS adjuvant activity, which genetic modification:
   (i) decreases or knocks-out expression of one or more of the following genes:
      (A) lpxL1 or a gene the sequence of which is at least 95% identical with SEQ ID NO:1;
      (B) lpxL2; and
      (C) lpxK;
   and/or
   (ii) effects expression of one or more of genes lpxE and/or pagL.

3. The process according to claim 1, wherein the time after onset of the stationary growth phase during which the bacteria are incubated in the medium in step (b) is between about 1 and 9 hours.

4. The process according to claim 1, further comprising a step of sterilizing the bacterial OMV.

5. The process according to claim 1, wherein the concentration of the metal chelating agent in step (b) is between about 5 mM and 15 mM, and/or wherein the pH is between:
   (i) pH 8.0 and pH 9.5, or
   (ii) pH 8.0 and pH 9.0, or
   (iii) pH 8.2 and pH 8.8, or
   (iv) pH 8.4 and pH 8.7.

6. The process according to claim 1, wherein the cultivating of step (a) and/or the incubating of step (b) is performed in a medium volume of at least about 10 liters.

7. The process according to claim 1, wherein the Gram-negative bacteria are a species of the genera *Neisseria* or *Bordetella*.

8. The process according to claim 1 wherein the Gram-negative bacteria comprise one or more mutations that decrease or knock-out expression of a gene product.

9. The process according to claim 1, wherein the Gram-negative bacteria are of multiple PorA subtypes.

10. The process according to claim 1, wherein the bacterial population comprises Gram-negative bacteria of more than one strain wherein bacteria of each strain are of different PorA subtypes.

11. The process according to claim 1, wherein the Gram-negative bacteria express an antigen that is foreign to the strain or species of said bacteria.

12. The process according to claim 1, further comprising a step of combining the recovered bacterial OMV with a pharmaceutically acceptable excipient.

13. The process according to claim 1 wherein the chelating agent is EDTA.

14. The process according to claim 3 wherein the time after onset of the stationary growth phase during which the bacteria are incubated in the medium in step (b) is between about 2 and 5 hours.

15. The process according to claim 7 wherein the bacterial species is *Neisseria meningitidis* or *Bordetella pertussis*.

16. The process according to claim 8 wherein the gene product whose expression is decreased or knocked out is Cps or a product active in lipid A biosynthesis selected from the group consisting of LpxL1, RmpM, PorA, PorB and OpA.

* * * * *